United States Patent
Mitchell et al.

(10) Patent No.: US 7,105,729 B2
(45) Date of Patent: Sep. 12, 2006

(54) COTTON CULTIVAR 00S07

(75) Inventors: James F. Mitchell, Cleveland, MS (US); Robert McGowen, Greenville, MS (US)

(73) Assignee: D&PL Technology Holding Company, LLC, Scott, MS (US)

( * ) Notice: Subject to any disclaimer, the term of this patent is extended or adjusted under 35 U.S.C. 154(b) by 122 days.

(21) Appl. No.: 10/900,696

(22) Filed: Jul. 27, 2004

(65) Prior Publication Data

US 2004/0255352 A1    Dec. 16, 2004

(51) Int. Cl.
*A01H 5/00*    (2006.01)
*A01H 5/10*    (2006.01)
*A01H 1/00*    (2006.01)
*A01H 4/00*    (2006.01)
*C12N 15/82*    (2006.01)

(52) U.S. Cl. .............. 800/314; 800/260; 800/266; 800/278; 800/279; 800/281; 800/295; 800/300; 800/301; 800/302; 800/303; 435/410

(58) Field of Classification Search .............. 800/260, 800/263, 264, 265, 266, 268, 269, 274, 277, 800/278, 279, 281, 284, 314; 435/410, 421, 435/427, 430, 430.1, 468
See application file for complete search history.

(56) References Cited

U.S. PATENT DOCUMENTS

| | | | |
|---|---|---|---|
| 5,304,719 A | | 4/1994 | Segebart |
| 5,367,109 A | | 11/1994 | Segebart |
| 5,523,520 A | | 6/1996 | Hunsperger et al. |
| 5,763,755 A | | 6/1998 | Carlone |
| 5,850,009 A | * | 12/1998 | Kevern ............... 800/271 |
| 2004/0250319 A1 | * | 12/2004 | McGowen et al. ...... 800/314 |

OTHER PUBLICATIONS

Fryxell. 1984. Cotton, Agronomy Monograph 24. Amer. Soc. Agron., Kohel and Lewis, eds., p. 53-54.*
Mishra et al. 2003. Plant Cell Tissue and Organ Culture 73: 21-35.*
Zeven et al. 1983. Euphytica 32: 319-327.*
Young et al. Theor. Appl. Genet. 1989. 77: 353-359.*
Ragot et al. 1994. Techniques et utilzations des margueurs moleculaires. p. 45-56.*
Allard, R. W., 1960. Selection under self-fertilization. In Principles of Plant Breeding, John Wiley & Sons, Inc., p. 55.
Eshed, et al., 1996. Less-than-additive epistatic interactions of quantitative trait loci in tomato. Genetics 143:1807-1817.
Fehr, W.R., 1987. Principles of cultivar development. In Theory and Technique, McGraw-Hill, Inc. 1:31-33.
Kraft, et al., 2000. Linkage disequilibrium and fingerprinting in surgar beet. Theor. Appl. Genet. 101:323-326.
Mishra, et al., 2003. Development of a highly regenerable elite acala cotton (*Gossypium hirsutum* cv. Maxxa)—a step towards genotype-independent regeneration. Plant Cell, Tissue and Organ Culture 73:21-35.
Sahkanokho, et al., 2001. Induction of highly embryogenic calli and plant regeneration in upland (*Gossypium hirsutum* L.) and pima (*Gossypium barbadense* L.) cottons. Crop Sci. 41:1235-1240.
Wilson, R. Douglas, 1989. Yield, earliness, and fiber properties of cotton carrying combined traits for pink bollworm resistance. Crop Sci. 29:7-12.
Fryxell, P.A., 1984. Taxonomy and Germplasm resources. In Cotton Monograph 24. Amer. Soc. Agron., Kohel, R.J. and C.F. Lewis, eds., p. 53-54.
Ragot, M., et al., 1994. Marker-assisted backcrossing: a practical example. In Techniques et utilizations des marqueurs moleculaires. Montpellier, France, p. 45-56.
Young, N.D. and S.D. Tanksley, 1989. RFLP analysis of the size of chromosomal segments retained around the Tm-2 locus of tomato during backcross breeding. Theor. Appl. Genet. 77:353-359.
Zeven, A.C., et al., 1983. Investigation of linkage drag in near isogenic lines of wheat by testing for seedling reaction to races of stem rust, leaf rust and yellow rust. Euphytica 32:319-327.

* cited by examiner

*Primary Examiner*—David H. Kruse
*Assistant Examiner*—Keith O. Robinson
(74) *Attorney, Agent, or Firm*—Jondle & Associates P.C.

(57) ABSTRACT

A cotton cultivar, designated 00S07, is disclosed. The invention relates to the seeds of cotton cultivar 00S07, to the plants of cotton 00S07 and to methods for producing a cotton plant produced by crossing the cultivar 00S07 with itself or another cotton variety. The invention further relates to hybrid cotton seeds and plants produced by crossing the cultivar 00S07 with another cotton cultivar.

25 Claims, No Drawings

COTTON CULTIVAR 00S07

BACKGROUND OF THE INVENTION

The present invention relates to a cotton (*Gossypium*) seed, a cotton plant, a cotton variety and a cotton hybrid. This invention further relates to a method for producing cotton seed and plants.

There are numerous steps in the development of any novel, desirable plant germplasm. Plant breeding begins with the analysis and definition of problems and weaknesses of the current germplasm, the establishment of program goals, and the definition of specific breeding objectives. The next step is selection of germplasm that possess the traits to meet the program goals. The goal is to combine in a single variety an improved combination of desirable traits from the parental germplasm. In cotton, the important traits include higher fiber (lint) yield, earlier maturity, improved fiber quality, resistance to diseases and insects, resistance to drought and heat, and improved agronomic traits.

Pureline cultivars of cotton are commonly bred by hybridization of two or more parents followed by selection. The complexity of inheritance, the breeding objectives and the available resources influence the breeding method. Pedigree breeding, recurrent selection breeding and backcross breeding are breeding methods commonly used in self pollinated crops such as cotton. These methods refer to the manner in which breeding pools or populations are made in order to combine desirable traits from two or more cultivars or various broad-based sources. The procedures commonly used for selection of desirable individuals or populations of individuals are called mass selection, plant-to-row selection and single seed descent or modified single seed descent. One, or a combination of these selection methods, can be used in the development of a cultivar from a breeding population.

Pedigree breeding is primarily used to combine favorable genes into a totally new cultivar that is different in many traits than either parent used in the original cross. It is commonly used for the improvement of self-pollinating crops. Two parents which possess favorable, complementary traits are crossed to produce an $F_1$ (filial generation 1). An $F_2$ population is produced by selfing $F_1$ plants. Selection of desirable individual plants may begin as early as the $F_2$ generation wherein maximum gene segregation occurs. Individual plant selection can occur for one or more generations. Successively, seed from each selected plant can be planted in individual, identified rows or hills, known as progeny rows or progeny hills, to evaluate the line and to increase the seed quantity, or, to further select individual plants. Once a progeny row or progeny hill is selected as having desirable traits it becomes what is known as a breeding line that is specifically identifiable from other breeding lines that were derived from the same original population. At an advanced generation (i.e., $F_5$ or higher) seed of individual lines are evaluated in replicated testing. At an advanced stage the best lines or a mixture of phenotypically similar lines from the same original cross are tested for potential release as new cultivars.

Descriptions of other breeding methods that are commonly used for different traits and crops can be found in one of several reference books (e.g., Allard, 1960; Simmonds, 1979; Sneep, et al. 1979; Fehr, 1987).

The single seed descent procedure in the strict sense refers to planting a segregating population, harvesting one seed from every plant, and combining these seeds into a bulk which is planted the next generation. When the population has been advanced to the desired level of inbreeding, the plants from which lines are derived will each trace to different $F_2$ individuals. Primary advantages of the seed descent procedures are to delay selection until a high level of homozygosity (e.g., lack of gene segregation) is achieved in individual plants, and to move through these early generations quickly, usually through using winter nurseries.

The modified single seed descent procedures involve harvesting multiple seed (i.e., a single lock or a simple boll) from each plant in a population and combining them to form a bulk. Part of the bulk is used to plant the next generation and part is put in reserve. This procedure has been used to save labor at harvest and to maintain adequate seed quantities of the population.

Selection for desirable traits can occur at any segregating generation ($F_2$ and above). Selection pressure is exerted on a population by growing the population in an environment where the desired trait is maximally expressed and the individuals or lines possessing the trait can be identified. For instance, selection can occur for disease resistance when the plants or lines are grown in natural or artificially-induced disease environments, and the breeder selects only those individuals having little or no disease and are thus assumed to be resistant.

Promising advanced breeding lines are thoroughly tested and compared to popular cultivars in environments representative of the commercial target area(s) for three or more years. The best lines having superiority over the popular cultivars are candidates to become new commercial cultivars. Those lines still deficient in a few traits are discarded or utilized as parents to produce new populations for further selection.

These processes, which lead to the final step of marketing and distribution, usually take from seven to twelve years from the time the first cross is made. Therefore, development of new cultivars is a time-consuming process that requires precise forward planning, efficient use of resources, and a minimum of changes in direction.

A most difficult task is the identification of individuals that are genetically superior because, for most traits the true genotypic value is masked by other confounding plant traits or environmental factors. One method of identifying a superior plant is to observe its performance relative to other experimental lines and widely grown standard cultivars. For many traits a single observation is inconclusive, and replicated observations over time and space are required to provide a good estimate of a line's genetic worth.

The goal of a commercial cotton breeding program is to develop new, unique and superior cotton cultivars. The breeder initially selects and crosses two or more parental lines, followed by generation advancement and selection, thus producing many new genetic combinations. The breeder can theoretically generate billions of different genetic combinations via this procedure. The breeder has no direct control over which genetic combinations will arise in the limited population size which is grown. Therefore, two breeders will never develop the same line having the same traits.

Each year, the plant breeder selects the germplasm to advance to the next generation. This germplasm is grown under unique and different geographical, climatic and soil conditions, and further selections are then made, during and at the end of the growing season. The lines which are developed are unpredictable. This unpredictability is because the breeder's selection occurs in unique environments, with no control at the DNA level (using conventional breeding procedures), and with millions of different possible genetic combinations being generated. A breeder of ordinary skill in the art cannot predict the final resulting lines he develops, except possibly in a very gross and general fashion. The same breeder cannot produce, with any reasonable likelihood, the same cultivar twice by using the exact same original parents and the same selection techniques. This unpredictability results in the expenditure of large amounts of research moneys to develop superior new cotton cultivars.

Proper testing should detect any major faults and establish the level of superiority or improvement over current cultivars. In addition to showing superior performance, there must be a demand for a new cultivar that is compatible with industry standards or which creates a new market. The introduction of a new cultivar will incur additional costs to the seed producer, and the grower, processor and consumer; for special advertising and marketing and commercial production practices, and new product utilization. The testing preceding the release of a new cultivar should take into consideration research and development costs as well as technical superiority of the final cultivar. For seed-propagated cultivars, it must be feasible to produce seed easily and economically.

Cotton, *Gossypium hirsutum*, is an important and valuable field crop. Thus, a continuing goal of plant breeders is to develop stable, high yielding cotton cultivars that are agronomically sound. The reasons for this goal are obviously to maximize the amount and quality of the fiber produced on the land used and to supply fiber, oil and food for animals and humans. To accomplish this goal, the cotton breeder must select and develop plants that have the traits that result in superior cultivars.

The development of new cotton cultivars requires the evaluation and selection of parents and the crossing of these parents. The lack of predictable success of a given cross requires that a breeder, in any given year, make several crosses with the same or different breeding objectives.

The cotton flower is monecious in that the male and female structures are in the same flower. The crossed or hybrid seed is produced by manual crosses between selected parents. Floral buds of the parent that is to be the female are emasculated prior to the opening of the flower by manual removal of the male anthers. At flowering, the pollen from flowers of the parent plants designated as male, are manually placed on the stigma of the previous emasculated flower. Seed developed from the cross is known as first generation ($F_1$) hybrid seed. Planting of this seed produces $F_1$ hybrid plants of which half their genetic component is from the female parent and half from the male parent. Segregation of genes begins at meiosis thus producing second generation ($F_2$) seed. Assuming multiple genetic differences between the original parents, each $F_2$ seed has a unique combination of genes.

SUMMARY OF THE INVENTION

The present invention relates to a cotton seed, a cotton plant, a cotton variety and a method for producing a cotton plant.

The present invention further relates to a method of producing cotton seeds and plants by crossing a plant of the instant invention with another cotton plant.

This invention further relates to the seeds of cotton variety 00S07, to the plants of cotton variety 00S07 and to methods for producing a cotton plant produced by crossing the cotton 00S07 with itself or another cotton line. Thus, any such methods using the cotton variety 00S07 are part of this invention, including selfing, backcrosses, hybrid production, crosses to populations, and the like.

In another aspect, the present invention provides for single trait converted plants of 00S07. The single transferred trait may preferably be a dominant or recessive allele. Preferably, the single transferred trait will confer such traits as herbicide resistance, insect resistance, resistance for bacterial, fungal, or viral disease, male fertility, male sterility, enhanced fiber quality, and industrial usage. The single trait may be a naturally occurring cotton gene or a transgene introduced through genetic engineering techniques.

In another aspect, the present invention provides regenerable cells for use in tissue culture of cotton plant 00S07. The tissue culture will preferably be capable of regenerating plants having the physiological and morphological characteristics of the foregoing cotton plant, and of regenerating plants having substantially the same genotype as the foregoing cotton plant. Preferably, the regenerable cells in such tissue cultures will be embryos, protoplasts, meristematic cells, callus, pollen, leaves, anthers, roots, root tips, flowers, seeds, or stems. Still further, the present invention provides cotton plants regenerated from the tissue cultures of the invention.

DEFINITIONS

In the description and tables which follow, a number of terms are used. In order to provide a clear and consistent understanding of the specification and claims, including the scope to be given such terms, the following definitions are provided:

Lint Yield. As used herein, the term "lint yield" is defined as the measure of the quantity of fiber produced on a given unit of land. Presented below in pounds of lint per acre.

Lint Percent (Lint %). As used herein, the term "lint percent" is defined as the lint (fiber) fraction of seed cotton (lint and seed).

Gin Turnout. As used herein, the term "gin turnout" is defined as a fraction of lint in a machine harvested sample of seed cotton (lint, seed, and trash).

Fiber Length (Len). As used herein, the term "fiber length" is defined as 2.5% span length in inches of fiber as measured by High Volume Instrumentation (HVI).

Uniformity Ratio (UR). As used herein, the term "uniformity ratio" is defined as a measure of the relative length uniformity of a bundle of fibers as measured by HVI.

Micronaire (Mic). As used herein, the term "micronaire" is defined as a measure of the fineness of the fiber. Within a cotton cultivar, micronaire is also a measure of maturity. Micronaire differences are governed by changes in perimeter or in cell wall thickness, or by changes in both. Within a variety, cotton perimeter is fairly constant and maturity will cause a change in micronaire. Consequently, micronaire has a high correlation with maturity within a variety of cotton. Maturity is the degree of development of cell wall thickness. Micronaire may not have a good correlation with maturity between varieties of cotton having different fiber perimeter. Micronaire values range from about 2.0 to 6.0:

| | | |
|---|---|---|
| Below 2.9 | Very fine | Possible small perimeter but mature (good fiber), or large perimeter but immature (bad fiber). |
| 2.9 to 3.7 | Fine | Various degrees of maturity and/or perimeter. |
| 3.8 to 4.6 | Average | Average degree of maturity and/or perimeter. |
| 4.7 to 5.5 | Coarse | Usually fully developed (mature), but larger perimeter. |
| 5.6+ | Very coarse | Fully developed, large-perimeter fiber. |

Fiber Strength (T1). As used herein, the term "fiber strength" is defined as the force required to break a bundle of fibers as measured in grams per millitex on the HVI.

Fiber Elongation (E1). As used herein, the term "fiber elongation" is defined as the measure of elasticity of a bundle of fibers as measured by HVI.

Plant Height (Hgt). As used herein, the term "plant height" is defined as the average height in inches or centimeters of a group of plants.

Stringout Ratinq (So). As used herein, the term "stringout rating" is defined as a visual rating prior to harvest of the relative looseness of the seed cotton held in the boll structure on the plant.

Maturity Rating (Mat). As used herein, the term "maturity rating" is defined as a visual rating near harvest on the amount of opened bolls on the plant.

Vegetative Nodes. As used herein, the term "vegetative nodes" is defined as the number of nodes from the cotyledonary node to the first fruiting branch on the main stem of the plant.

Seedweight (Sdwt). As used herein, the term "seedweight" is the weight of 100 seeds in grams.

Fallout (Fo). As used herein, the term "fallout" refers to the rating of how much cotton has fallen on the ground at harvest.

Lint Index. As used herein, the term "lint index" refers to the weight of lint per seed in milligrams.

Seed/boll. As used herein, the term "seed/boll" refers to the number of seeds per boll.

Seedcotton/boll. As used herein, the term "seedcotton/boll" refers to the weight of seedcotton per boll.

Lint/boll. As used herein, the term "lint/boll" is the weight of lint per boll.

Fruiting Nodes. As used herein, the term "fruiting nodes" is defined as the number of nodes on the main stem from which arise branches which bear fruit or bolls.

Essentially all the physiological and morphological characteristics. A plant having essentially all the physiological and morphological characteristics means a plant having the physiological and morphological characteristics, except for the characteristics derived from the converted trait.

Single trait Converted (Conversion). Single trait converted (conversion) plant refers to plants which are developed by a plant breeding technique called backcrossing or via genetic engineering wherein essentially all of the desired morphological and physiological characteristics of a variety are recovered in addition to the single trait transferred into the variety via the backcrossing technique or via genetic engineering.

Disease Resistance. As used herein, the term "disease resistance" is defined as the ability of plants to restrict the activities of a specified pest, such as an insect, fungus, virus, or bacterial.

Disease Tolerance. As used herein, the term "disease tolerance" is defined as the ability of plants to endure a specified pest (such as an insect, fungus, virus or bacteria) or an adverse environmental condition and still perform and produce in spite of this disorder.

VRDP. As used herein, the term "VRDP" is defined as the allele designation for the single dominant allele of the present invention which confers virus resistance. VRDP designates "Virus Resistance Deltapine".

TABLE 1

VARIETY DESCRIPTION INFORMATION

Species: *Gossypium hirsutum* L.
General:

Plant Habit: Intermediate
Foliage: Sparse
Stem Lodging: Intermediate
Fruiting Branch: Normal
Growth: Intermediate
Leaf Color: Light green
Boll Shape: Length > Width
Boll Breadth: Broadest at base
Leaf (Upper most, fully expanded leaf):

Type: Normal
Pubescence: Medium
Nectaries: Present
Stem Pubescence: Intermediate
Glands:

Leaf: Normal
Stem: Normal
Calyx Lobe: Normal
Flower:

Petals: Cream
Pollen: Cream
Petal Spot: Absent
Boll:

Gin Turnout: Picked 38.8
Fiber Properties:

Length (inches, 2.5% SL): 1.20
Uniformity (%): 84.24
Strength, T1 (g/tex): 31.92
Elongation, E1 (%): 10.68
Micronaire: 4.02
Nematodes, Insects and Pests:

| | |
|---|---|
| Boll Weevil | Susceptible |
| Bollworm | Susceptible |
| Cotton Aphid | Susceptible |
| Fall Armyworm | Susceptible |
| Pink Bollworm | Susceptible |
| Tobacco Bud Worm | Susceptible |

This invention is also directed to methods for producing a cotton plant by crossing a first parent cotton plant with a second parent cotton plant, wherein the first or second cotton plant is the cotton plant from the line 00S07. Further, both the first and second parent cotton plants may be the cultivar 00S07 (e.g., self-pollination). Therefore, any methods using the cultivar 00S07 are part of this invention: selfing, backcrosses, hybrid breeding, and crosses to populations. Any plants produced using cultivar 00S07 as a parent are within the scope of this invention. As used herein, the term "plant" includes plant cells, plant protoplasts, plant cells of tissue culture from which cotton plants can be regenerated, plant calli, plant clumps, and plant cells that are intact in plants or parts of plants, such as pollen, flowers, embryos, ovules, seeds, pods, leaves, stems, roots, anthers and the like. Thus, another aspect of this invention is to provide for cells which upon growth and differentiation produce a cultivar having essentially all of the physiological and morphological characteristics of 00S07.

Culture for expressing desired structural genes and cultured cells are known in the art. Also as known in the art, cotton is transformable and regenerable such that whole plants containing and expressing desired genes under regulatory control may be obtained. General descriptions of plant expression vectors and reporter genes and transformation protocols can be found in Gruber, et al., "Vectors for Plant Transformation, in Methods in Plant Molecular Biology & Biotechnology" in Glich, et al., (Eds. pp. 89–119, CRC Press, 1993). Moreover GUS expression vectors and GUS gene cassettes are available from Clone Tech Laboratories, Inc., Palo Alto, Calif. while luciferase expression vectors and luciferase gene cassettes are available from Promega Corp. (Madison, Wis.). General methods of culturing plant tissues are provided for example by Maki, et al., "Procedures for Introducing Foreign DNA into Plants" in Methods in Plant Molecular Biology & Biotechnology, Glich, et al., (Eds. pp. 67–88 CRC Press, 1993); and by Phillips, et al., "Cell-Tissue Culture and In-Vitro Manipulation" in Corn & Corn Improvement, 3rd Edition; Sprague, et al., (Eds. pp. 345–387) American Society of Agronomy Inc., 1988. Methods of introducing expression vectors into plant tissue include the direct infection or co-cultivation of plant cells with *Agrobacterium tumefaciens*, Horsch et al., Science, 227:1229 (1985). Descriptions of *Agrobacterium* vectors systems and methods for *Agrobacterium*-mediated gene transfer provided by Gruber, et al., supra.

Useful methods include, but are not limited, to expression vectors introduced into plant tissues using a direct gene transfer method such as microprojectile-mediated delivery, DNA injection, electroporation and the like. More preferably, expression vectors are introduced into plant tissues using the microprojectile media delivery with the biolistic device *Agrobacterium*-medicated transformation. Transformant plants obtained with the protoplasm of the invention are intended to be within the scope of this invention.

The present invention contemplates a cotton plant regenerated from a tissue culture of a variety (e.g., 00S07) or hybrid plant of the present invention. As is well known in the art, tissue culture of cotton can be used for the in vitro regeneration of a cotton plant. Tissue culture of various tissues of cotton and regeneration of plants therefrom is well known and widely published.

When the term cotton plant is used in the context of the present invention, this also includes any single trait conversions of that variety. The term single trait converted plant as used herein refers to those cotton plants which are developed by a plant breeding technique called backcrossing or via genetic engineering wherein essentially all of the desired morphological and physiological characteristics of a variety are recovered in addition to the single trait transferred into the variety. Backcrossing methods can be used with the present invention to improve or introduce a characteristic into the variety. The term backcrossing as used herein refers to the repeated crossing of a hybrid progeny back to the recurrent parent. The parental cotton plant which contributes the trait for the desired characteristic is termed the nonrecurrent or donor parent. This terminology refers to the fact that the nonrecurrent parent is used one time in the backcross protocol and therefore does not recur. The parental cotton plant to which the trait or traits from the nonrecurrent parent are transferred is known as the recurrent parent as it is used for several rounds in the backcrossing protocol (Poehiman & Sleper, 1994; Fehr, 1987). In a typical backcross protocol, the original variety of interest (recurrent parent) is crossed to a second variety (nonrecurrent parent) that carries the single gene of interest to be transferred. The resulting progeny from this cross are then crossed again to the recurrent parent and the process is repeated until a cotton plant is obtained wherein essentially all of the desired morphological and physiological characteristics of the recurrent parent are recovered in the converted plant, in addition to the single transferred gene from the nonrecurrent parent.

The selection of a suitable recurrent parent is an important step for a successful backcrossing procedure. The goal of a backcross protocol is to alter or substitute a single trait or characteristic in the original variety. To accomplish this, a gene or genes of the recurrent variety are modified or substituted with the desired gene(s) from the nonrecurrent parent, while retaining essentially all of the rest of the desired genetic, and therefore the desired physiological and morphological, constitution of the original variety. The choice of the particular nonrecurrent parent will depend on the purpose of the backcross. One of the major purposes is to add some commercially desirable, agronomically important trait to the plant. The exact backcrossing protocol will depend on the characteristic or trait being altered to determine an appropriate testing protocol. Although backcrossing methods are simplified when the characteristic being transferred is a dominant allele, a recessive allele may also be transferred. In this instance it may be necessary to introduce a test of the progeny to determine if the desired characteristic has been successfully transferred.

Many traits have been identified that are not regularly selected for in the development of a new variety but that can be improved by backcrossing techniques. Traits may or may not be transgenic, examples of these traits include but are not limited to, male sterility, herbicide resistance, resistance for bacterial, fungal, or viral disease, insect resistance, male fertility, enhanced fiber quality, industrial usage, yield stability and yield enhancement. These traits are generally inherited through the nucleus.

FURTHER EMBODIMENTS OF THE INVENTION

With the advent of molecular biological techniques that have allowed the isolation and characterization of genes that encode specific protein products, scientists in the field of plant biology developed a strong interest in engineering the genome of plants to contain and express foreign genes, or additional, or modified versions of native, or endogenous, genes (perhaps driven by different promoters) in order to alter the traits of a plant in a specific manner. Such foreign additional and/or modified genes are referred to herein collectively as "transgenes". Over the last fifteen to twenty years several methods for producing transgenic plants have been developed, and the present invention, in particular embodiments, also relates to transformed versions of the claimed variety or line.

Plant transformation involves the construction of an expression vector which will function in plant cells. Such a vector comprises DNA comprising a gene under control of or operatively linked to a regulatory element (for example, a promoter). The expression vector may contain one or more such operably linked gene/regulatory element combinations. The vector(s) may be in the form of a plasmid, and can be used alone or in combination with other plasmids, to provide transformed cotton plants, using transformation methods as described below to incorporate transgenes into the genetic material of the cotton plant(s).

Expression Vectors for Cotton Transformation: Marker Genes—Expression vectors include at least one genetic marker, operably linked to a regulatory element (a promoter, for example) that allows transformed cells containing the marker to be either recovered by negative selection, i.e., inhibiting growth of cells that do not contain the selectable marker gene, or by positive selection, i.e., screening for the product encoded by the genetic marker. Many commonly used selectable marker genes for plant transformation are well known in the transformation arts, and include, for example, genes that code for enzymes that metabolically detoxify a selective chemical agent which may be an antibiotic or a herbicide, or genes that encode an altered target which is insensitive to the inhibitor. A few positive selection methods are also known in the art.

One commonly used selectable marker gene for plant transformation is the neomycin phosphotransferase II (nptII) under the control of plant regulatory signals which confers resistance to kanamycin. Fraley et al., *Proc. Natl. Acad. Sci. U.S.A.*, 80:4803 (1983). Another commonly used selectable marker gene is the hygromycin phosphotransferase gene which confers resistance to the antibiotic hygromycin. Vanden Elzen et al., *Plant Mol. Biol.*, 5:299 (1985).

Additional selectable marker genes of bacterial origin that confer resistance to antibiotics include gentamycin acetyl transferase, streptomycin phosphotransferase, aminoglycoside-3'-adenyl transferase, the bleomycin resistance determinant. Hayford et al., *Plant Physiol.* 86:1216 (1988), Jones et al., *Mol. Gen. Genet.*, 210:86 (1987), Svab et al., *Plant Mol. Biol.* 14:197 (1990) Hille et al., *Plant Mol. Biol.* 7:171 (1986). Other selectable marker genes confer resistance to herbicides such as glyphosate, glufosinate or broxynil. Comai et al., *Nature* 317:741–744 (1985), Gordon-Kamm et al., *Plant Cell* 2:603–618 (1990) and Stalker et al., *Science* 242:419–423 (1988).

Other selectable marker genes for plant transformation are not of bacterial origin. These genes include, for example, mouse dihydrofolate reductase, plant 5-enolpyruvylshikimate-3-phosphate synthase and plant acetolactate synthase. Eichholtz et al., *Somatic Cell Mol. Genet.* 13:67 (1987), Shah et al., *Science* 233:478 (1986), Charest et al., *Plant Cell Rep.* 8:643 (1990).

Another class of marker genes for plant transformation require screening of presumptively transformed plant cells rather than direct genetic selection of transformed cells for resistance to a toxic substance such as an antibiotic. These genes are particularly useful to quantify or visualize the spatial pattern of expression of a gene in specific tissues and are frequently referred to as reporter genes because they can be fused to a gene or gene regulatory sequence for the investigation of gene expression. Commonly used genes for screening presumptively transformed cells include β-glucuronidase (GUS, β-galactosidase, luciferase and chloramphenicol, acetyltransferase. Jefferson, R. A., *Plant Mol. Biol. Rep.* 5:387 (1987), Teeri et al., *EMBO J.* 8:343 (1989), Koncz et al., *Proc. Natl. Acad. Sci U.S.A.* 84:131 (1987), DeBlock et al., *EMBO J.* 3:1681 (1984).

Recently, in vivo methods for visualizing GUS activity that do not require destruction of plant tissue have been made available. Molecular Probes publication 2908, Imagene Green™, p. 1–4 (1993) and Naleway et al., *J. Cell Biol.* 115:151a (1991). However, these in vivo methods for visualizing GUS activity have not proven useful for recovery of transformed cells because of low sensitivity, high fluorescent backgrounds and limitations associated with the use of luciferase genes as selectable markers.

More recently, a gene encoding Green Fluorescent Protein (GFP) has been utilized as a marker for gene expression in prokaryotic and eukaryotic cells. Chalfie et al., *Science* 263:802 (1994). GFP and mutants of GFP may be used as screenable markers.

Promoters—Genes included in expression vectors must be driven by a nucleotide sequence comprising a regulatory element, for example, a promoter. Several types of promoters are now well known in the transformation arts, as are other regulatory elements that can be used alone or in combination with promoters.

As used herein, "promoter" includes reference to a region of DNA upstream from the start of transcription and involved in recognition and binding of RNA polymerase and other proteins to initiate transcription. A "plant promoter" is a promoter capable of initiating transcription in plant cells. Examples of promoters under developmental control include promoters that preferentially initiate transcription in certain tissues, such as leaves, roots, seeds, fibers, xylem vessels, tracheids, or sclerenchyma. Such promoters are referred to as "tissue-preferred". Promoters which intitiate transcription only in certain tissue are referred to as "tissue-specific". A "cell type" specific promoter primarily drives expression in certain cell types in one or more organs, for example, vascular cells in roots or leaves. An "inducible" promoter is a promoter which is under environmental control. Examples of environmental conditions that may effect transcription by inducible promoters include anaerobic conditions or the presence of light. Tissue-specific, tissue-preferred, cell type specific, and inducible promoters constitute the class of "non-constitutive" promoters. A "constitutive" promoter is a promoter which is active under most environmental conditions.

A. Inducible Promoters—An inducible promoter is operably linked to a gene for expression in cotton. Optionally, the inducible promoter is operably linked to a nucleotide sequence encoding a signal sequence which is operably linked to a gene for expression in cotton. With an inducible promoter the rate of transcription increases in response to an inducing agent.

Any inducible promoter can be used in the instant invention. See Ward et al., *Plant Mol. Biol.* 22:361–366 (1993). Exemplary inducible promoters include, but are not limited to, that from the ACEI system which responds to copper (Mett et al., *PNAS* 90:4567–4571 (1993)); In2 gene from maize which responds to benzenesulfonamide herbicide safeners (Hershey et al., *Mol. Gen Genetics* 227:229–237 (1991) and Gatz et al., *Mol. Gen. Genetics* 243:32–38 (1994)) or Tet repressor from Tn10 (Gatz et al., *Mol. Gen. Genetics* 227:229–237 (1991). A particularly preferred inducible promoter is a promoter that responds to an inducing agent to which plants do not normally respond. An exemplary inducible promoter is the inducible promoter from a steroid hormone gene, the transcriptional activity of which is induced by a glucocorticosteroid hormone. Schena et al., *Proc. Natl. Acad. Sci. U.S.A.* 88:0421 (1991).

B. Constitutive Promoters—A constitutive promoter is operably linked to a gene for expression in cotton or the constitutive promoter is operably linked to a nucleotide sequence encoding a signal sequence which is operably linked to a gene for expression in cotton.

Many different constitutive promoters can be utilized in the instant invention. Exemplary constitutive promoters include, but are not limited to, the promoters from plant viruses such as the 35S promoter from CaMV (Odell et al., *Nature* 313:810–812 (1985) and the promoters from such genes as rice actin (McElroy et al., *Plant Cell* 2:163–171 (1990)); ubiquitin (Christensen et al., *Plant Mol. Biol.* 12:619–632 (1989) and Christensen et al., *Plant Mol. Biol.* 18:675–689 (1992)); pEMU (Last et al., *Theor. Appl. Genet.* 81:581–588 (1991)); MAS (Velten et al., *EMBO J.* 3:2723–2730 (1984)) and maize H3 histone (Lepetit et al., *Mol. Gen. Genetics* 231:276–285 (1992) and Atanassova et al., *Plant Journal* 2 (3): 291–300 (1992)).

The ALS promoter, Xba1/NcoI fragment 5' to the *Brassica napus* ALS3 structural gene (or a nucleotide sequence similarity to said Xba1/NcoI fragment), represents a particularly useful constitutive promoter. See PCT application WO 96/30530.

C. Tissue-specific or Tissue-preferred Promoters—A tissue-specific promoter is operably linked to a gene for expression in cotton. Optionally, the tissue-specific promoter is operably linked to a nucleotide sequence encoding a signal sequence which is operably linked to a gene for expression in cotton. Plants transformed with a gene of interest operably linked to a tissue-specific promoter produce the protein product of the transgene exclusively, or preferentially, in a specific tissue.

Any tissue-specific or tissue-preferred promoter can be utilized in the instant invention. Exemplary tissue-specific or tissue-preferred promoters include, but are not limited to, a root-preferred promoter—such as that from the phaseolin gene (Murai et al., *Science* 23:476–482 (1983) and Sengupta-Gopalan et al., *Proc. Natl. Acad. Sci. U.S.A.* 82:3320–3324 (1985)); a leaf-specific and light-induced promoter such as that from cab or rubisco (Simpson et al., *EMBO J.* 4(11):2723–2729 (1985) and Timko et al., *Nature* 318:579–582 (1985)); an anther-specific promoter such as that from LAT52 (Twell et al., *Mol. Gen. Genetics* 217: 240–245 (1989)); a pollen-specific promoter such as that from Zm13 (Guerrero et al., *Mol. Gen. Genetics* 244: 161–168 (1993)) or a microspore-preferred promoter such as that from apg (Twell et al., *Sex. Plant Reprod.* 6:217–224 (1993). Signal Sequences for Targeting Proteins to Subcellular Compartments Transport of protein produced by transgenes to a subcellular compartment such as the chloroplast, vacuole, peroxisome, glyoxysome, cell wall or mitochondrion or for secretion into the apoplast, is accomplished by means of operably linking the nucleotide sequence encoding a signal sequence to the 5' and/or 3' region of a gene encoding the protein of interest. Targeting sequences at the 5' and/or 3' end of the structural gene may determine, during protein synthesis and processing, where the encoded protein is ultimately compartmentalized.

The presence of a signal sequence directs a polypeptide to either an intracellular organelle or subcellular compartment or for secretion to the apoplast. Many signal sequences are known in the art. See, for example Becker et al., *Plant Mol. Biol.* 20:49 (1992), Close, P. S., Master's Thesis, Iowa State University (1993), Knox, C., et al., "Structure and Organization of Two Divergent Alpha-Amylase Genes from Barley", *Plant Mol. Biol.* 9:3–17 (1987), Lerner et al., *Plant Physiol.* 91:124–129 (1989), Fontes et al., *Plant Cell* 3:483–496 (1991), Matsuoka et al., *Proc. Natl. Acad. Sci.* 88:834 (1991), Gould et al., *J. Cell. Biol.* 108:1657 (1989), Creissen et al., *Plant J.* 2:129 (1991), Kalderon, et al., A short amino acid sequence able to specify nuclear location, *Cell* 39:499–509 (1984), Steifel, et al., Expression of a maize cell wall hydroxyproline-rich glycoprotein gene in early leaf and root vascular differentiation, *Plant Cell* 2:785–793 (1990).

Foreign Protein Genes and Agronomic Genes—With transgenic plants according to the present invention, a foreign protein can be produced in commercial quantities. Thus, techniques for the selection and propagation of transformed plants, which are well understood in the art, yield a plurality of transgenic plants which are harvested in a conventional manner, and a foreign protein then can be extracted from a tissue of interest or from total biomass. Protein extraction from plant biomass can be accomplished by known methods which are discussed, for example, by Heney and Orr, *Anal. Biochem.* 114:92–6 (1981).

According to a preferred embodiment, the transgenic plant provided for commercial production of foreign protein is a cotton plant. In another preferred embodiment, the biomass of interest is seed. For the relatively small number of transgenic plants that show higher levels of expression, a genetic map can be generated, primarily via conventional RFLP, PCR and SSR analysis, which identifies the approximate chromosomal location of the integrated DNA molecule. For exemplary methodologies in this regard, see Glick and Thompson, Methods in Plant Molecular Biology and Biotechnology *CRC Press, Boca Raton* 269:284 (1993). Map information concerning chromosomal location is useful for proprietary protection of a subject transgenic plant. If unauthorized propagation is undertaken and crosses made with other germplasm, the map of the integration region can be compared to similar maps for suspect plants, to determine if the latter have a common parentage with the subject plant. Map comparisons would involve hybridizations, RFLP, PCR, SSR and sequencing, all of which are conventional techniques.

Likewise, by means of the present invention, agronomic genes can be expressed in transformed plants. More particularly, plants can be genetically engineered to express various phenotypes of agronomic interest. Exemplary genes implicated in this regard include, but are not limited to, those categorized below:

Genes that Confer Resistance to Pests or Disease and that Encode:

A. Plant disease resistance genes. Plant defenses are often activated by specific interaction between the product of a disease resistance gene (R) in the plant and the product of a corresponding avirulence (Avr) gene in the pathogen. A plant variety can be transformed with cloned resistance gene to engineer plants that are resistant to specific pathogen strains. See, for example Jones et al., *Science* 266:789 (1994) (cloning of the tomato Cf-9 gene for resistance to *Cladosporium fulvum*); Martin et al., *Science* 262:1432 (1993) (tomato Pto gene for resistance to *Pseudomonas syringae* pv. Tomato encodes a protein kinase); Mindrinos et al., *Cell* 78:1089 (1994) (*Arabidopsis* RSP2 gene for resistance to *Pseudomonas syringae*).

B. A gene conferring resistance to a pest, such as nematodes. See e.g., PCT Application WO 96/30517; PCT Application WO 93/19181.

C. A *Bacillus thuringiensis* protein, a derivative thereof or a synthetic polypeptide modeled thereon. See, for example, Geiser et al., *Gene* 48:109 (1986), who disclose the cloning and nucleotide sequence of a Bt δ-endotoxin gene. Moreover, DNA molecules encoding δ-endotoxin genes can be purchased from American Type Culture Collection, Manassas, Va., for example, under ATCC Accession Nos. 40098, 67136, 31995 and 31998.

D. A lectin. See, for example, the disclosure by Van Damme et al., *Plant Molec. Biol.* 24:25 (1994), who disclose the nucleotide sequences of several *Clivia miniata* mannose-binding lectin genes.

E. A vitamin-binding protein such as avidin. See PCT application US93/06487, the contents of which are hereby incorporated by reference. The application teaches the use of avidin and avidin homologues as larvicides against insect pests.

F. An enzyme inhibitor, for example, a protease or proteinase inhibitor or an amylase inhibitor. See, for example, Abe et al., *J. Biol. Chem.* 262:16793 (1987) (nucleotide sequence of rice cysteine proteinase inhibitor), Huub et al., Plant Molec. Biol. 21:985 (1993) (nucleotide sequence of cDNA encoding tobacco proteinase inhibitor I), Sumitani et al., Biosci. Biotech. Biochem. 57:1243 (1993) (nucleotide sequence of *Streptomyces nitrosporeus* α-amylase inhibitor) and U.S. Pat. No. 5,494,813 (Hepher and Atkinson, issued Feb. 27, 1996).

G. An insect-specific hormone or pheromone such as an ecdysteroid and juvenile hormone, a variant thereof, a mimetic based thereon, or an antagonist or agonist thereof. See, for example, the disclosure by Hammock et al., *Nature* 344:458 (1990), of baculovirus expression of cloned juvenile hormone esterase, an inactivator of juvenile hormone.

H. An insect-specific peptide or neuropeptide which, upon expression, disrupts the physiology of the affected pest. For example, see the disclosures of Regan, *J. Biol. Chem.* 269:9 (1994) (expression cloning yields DNA coding for insect diuretic hormone receptor), and Pratt et al., *Biochem. Biophys. Res. Comm.* 163:1243 (1989) (an allostatin is identified in *Diploptera puntata*). See also U.S. Pat. No. 5,266,317 to Tomalski et al., who disclose genes encoding insect-specific, paralytic neurotoxins.

I. An insect-specific venom produced in nature by a snake, a wasp, etc. For example, see Pang et al., *Gene* 116:165 (1992), for disclosure of heterologous expression in plants of a gene coding for a scorpion insectotoxic peptide.

J. An enzyme responsible for a hyperaccumulation of a monterpene, a sesquiterpene, a steroid, hydroxamic acid, a phenylpropanoid derivative or another non-protein molecule with insecticidal activity.

K. An enzyme involved in the modification, including the post-translational modification, of a biologically active molecule; for example, a glycolytic enzyme, a proteolytic enzyme, a lipolytic enzyme, a nuclease, a cyclase, a transaminase, an esterase, a hydrolase, a phosphatase, a kinase, a phosphorylase, a polymerase, an elastase, a chitinase and a glucanase, whether natural or synthetic. See PCT application WO 93/02197 in the name of Scott et al., which discloses the nucleotide sequence of a callase gene. DNA molecules which contain chitinase-encoding sequences can be obtained, for example, from the ATCC under Accession Nos. 39637 and 67152. See also Kramer et al., *Insect Biochem. Molec. Biol.* 23:691 (1993), who teach the nucleotide sequence of a cDNA encoding tobacco hookworm chitinase, and Kawalleck et al., *Plant Molec. Biol.* 21:673 (1993), who provide the nucleotide sequence of the parsley ubil4-2 polyubiquitin gene.

L. A molecule that stimulates signal transduction. For example, see the disclosure by Botella et al., *Plant Molec. Biol.* 24:757 (1994), of nucleotide sequences for mung bean calmodulin cDNA clones, and Griess et al., *Plant Physiol.* 104:1467 (1994), who provide the nucleotide sequence of a maize calmodulin cDNA clone.

M. A hydrophobic moment peptide. See PCT application WO 95/16776 (disclosure of peptide derivatives of Tachyplesin which inhibit fungal plant pathogens) and PCT application WO 95/18855 (teaches synthetic antimicrobial peptides that confer disease resistance), the respective contents of which are hereby incorporated by reference.

N. A membrane permease, a channel former or a channel blocker. For example, see the disclosure of Jaynes et al., *Plant Sci* 89:43 (1993), of heterologous expression of a cecropin-β, lytic peptide analog to render transgenic tobacco plants resistant to *Pseudomonas solanacearum*.

O. A viral-invasive protein or a complex toxin derived therefrom. For example, the accumulation of viral coat proteins in transformed plant cells imparts resistance to viral infection and/or disease development effected by the virus from which the coat protein gene is derived, as well as by related viruses. See Beachy et al., *Ann. rev. Phytopathol.* 28:451 (1990). Coat protein-mediated resistance has been conferred upon transformed plants against alfalfa mosaic virus, cucumber mosaic virus, tobacco streak virus, potato virus X, potato virus Y, tobacco etch virus, tobacco rattle virus and tobacco mosaic virus. Id.

P. An insect-specific antibody or an immunotoxin derived therefrom. Thus, an antibody targeted to a critical metabolic function in the insect gut would inactivate an affected enzyme, killing the insect. Cf. Taylor et al., Abstract #497, Seventh Int'l Symposium on Molecular Plant-Microbe Interactions (Edinburgh, Scotland) (1994) (enzymatic inactivation in transgenic tobacco via production of single-chain antibody fragments).

Q. A virus-specific antibody. See, for example, Tavladoraki et al., *Nature* 366:469 (1993), who show that transgenic plants expressing recombinant antibody genes are protected from virus attack.

R. A developmental-arrestive protein produced in nature by a pathogen or a parasite. Thus, fungal endo α-1,4-D-polygalacturonases facilitate fungal colonization and plant nutrient release by solubilizing plant cell wall homo-α-1,4-D-galacturonase. See Lamb et al., *Bio/Technology* 10:1436 (1992). The cloning and characterization of a gene which encodes a bean endopolygalacturonase-inhibiting protein is described by Toubart et al., *Plant J.* 2:367 (1992).

S. A development-arrestive protein produced in nature by a plant. For example, Logemann et al., *Bio/Technology* 10:305 (1992), have shown that transgenic plants expressing the barley ribosome-inactivating gene have an increased resistance to fungal disease.

2. Genes that Confer Resistance to a Herbicide:

A. A herbicide that inhibits the growing point or meristem, such as an imidazolinone or a sulfonylurea. Exemplary genes in this category code for mutant ALS and AHAS enzyme as described, for example, by Lee et al., *EMBO J.* 7:1241 (1988), and Miki et al., *Theor. Appl. Genet.* 80:449 (1990), respectively.

B. Glyphosate (resistance impaired by mutant 5-enolpyruvl-3-phosphikimate synthase (EPSP) and aroA genes, respectively) and other phosphono compounds such as glufosinate (phosphinothricin acetyl transferase, PAT and *Streptomyces hygroscopicus* phosphinothricin-acetyl transferase, bar, genes), and pyridinoxy or phenoxy proprionic acids and cyclohexones (ACCase inhibitor-encoding genes). See, for example, U.S. Pat. No. 4,940,835 to Shah, et al., which discloses the nucleotide sequence of a form of EPSP which can confer glyphosate resistance. A DNA molecule encoding a mutant aroA gene can be obtained under ATCC accession number 39256, and the nucleotide sequence of the mutant gene is disclosed in U.S. Pat. No. 4,769,061 to Comai. European patent application No. 0 333 033 to Kumada et al., and U.S. Pat. No. 4,975,374 to Goodman et al., disclose nucleotide sequences of glutamine synthetase genes which confer resistance to herbicides such as L-phosphinothricin. The nucleotide sequence of a phosphinothricin-acetyl-transferase gene is provided in European application No. 0 242 246 to Leemans et al., DeGreef et al., *Bio/Technology* 7:61 (1989), describe the production of transgenic plants that express chimeric bar genes coding for phosphinothricin acetyl transferase activity. Exemplary of genes conferring resistance to phenoxy proprionic acids and cyclohexones, such as sethoxydim and haloxyfop are the Acc1-S1, Acc1-S2 and Acc1-S3 genes described by Marshall et al., *Theor. Appl. Genet.* 83:435 (1992).

C. A herbicide that inhibits photosynthesis, such as a triazine (psbA and gs+genes) and a benzonitrile (nitrilase gene). Przibila et al., *Plant Cell* 3:169 (1991), describe the transformation of Chlamydomonas with plasmids encoding mutant psbA genes. Nucleotide sequences for nitrilase genes are disclosed in U.S. Pat. No. 4,810,648 to Stalker, and DNA molecules containing these genes are available under ATCC Accession Nos. 53435, 67441, and 67442. Cloning and expression of DNA coding for a glutathione S-transferase is described by Hayes et al., *Biochem. J.* 285:173 (1992).

3. Genes that Confer or Contribute to a Value-Added Trait, Such as:

A. Modified fatty acid metabolism, for example, by transforming a plant with an antisense gene of stearoyl-ACP desaturase to increase stearic acid content of the plant. See Knultzon et al., *Proc. Natl. Acad. Sci. U.S.A.* 89:2624 (1992).

B. Decreased phytate content—1) Introduction of a phytase-encoding gene would enhance breakdown of phytate, adding more free phosphate to the transformed plant. For example, see Van Hartingsveldt et al., *Gene* 127:87 (1993), for a disclosure of the nucleotide sequence of an *Aspergillus niger* phytase gene. 2) A gene could be introduced that reduced phytate content. In maize, this, for example, could be accomplished, by cloning and then reintroducing DNA associated with the single allele which is responsible for maize mutants characterized by low levels of phytic acid. See Raboy et al., *Maydica* 35:383 (1990).

C. Modified carbohydrate composition effected, for example, by transforming plants with a gene coding for an enzyme that alters the branching pattern of starch. See Shiroza et al., *J. Bacteol.* 170:810 (1988) (nucleotide sequence of *Streptococcus mutants* fructosyltransferase gene), Steinmetz et al., *Mol. Gen. Genet.* 20:220 (1985) (nucleotide sequence of *Bacillus subtilis* levansucrase gene), Pen et al., *Bio/Technology* 10:292 (1992) (production of transgenic plants that express *Bacillus lichenifonnis* α-amylase), Elliot et al., *Plant Molec. Biol.* 21:515 (1993) (nucleotide sequences of tomato invertase genes), Sgaard et al., *J. Biol. Chem.* 268:22480 (1993) (site-directed mutagenesis of barley α-amylase gene), and Fisher et al., *Plant Physiol.* 102:1045 (1993) (maize endosperm starch branching enzyme II).

Methods for Cotton Transformation—Numerous methods for plant transformation have been developed, including biological and physical, plant transformation protocols. See, for example, Miki et al., "Procedures for Introducing Foreign DNA into Plants" in *Methods in Plant Molecular Biology and Biotechnology*, Glick B. R. and Thompson, J. E. Eds. (CRC Press, Inc., Boca Raton, 1993) pages 67–88. In addition, expression vectors and in vitro culture methods for plant cell or tissue transformation and regeneration of plants are available. See, for example, Gruber et al., "Vectors for Plant Transformation" in Methods in *Plant Molecular Biology and Biotechnology*, Glick B. R. and Thompson, J. E. Eds. (CRC Press, Inc., Boca Raton, 1993) pages 89–119.

A. *Agrobacterium*-mediated Transformation—One method for introducing an expression vector into plants is based on the natural transformation system of *Agrobacterium*. See, for example, Horsch et al., *Science* 227:1229 (1985). *A. tumefaciens* and *A. rhizogenes* are plant pathogenic soil bacteria which genetically transform plant cells. The Ti and Ri plasmids of *A. tumefaciens* and *A. rhizogenes*, respectively, carry genes responsible for genetic transformation of the plant. See, for example, Kado, C. I., *Crit. Rev. Plant Sci.* 10:1 (1991). Descriptions of *Agrobacterium* vector systems and methods for *Agrobacterium*-mediated gene transfer are provided by Gruber et al., supra, Miki et al., supra, and Moloney et al., *Plant Cell Reports* 8:238 (1989). See also, U.S. Pat. No. 5,563,055 (Townsend and Thomas), issued Oct. 8, 1996.

B. Direct Gene Transfer—Several methods of plant transformation, collectively referred to as direct gene transfer, have been developed as an alternative to *Agrobacterium*-mediated transformation. A generally applicable method of plant transformation is microprojectile-mediated transformation wherein DNA is carried on the surface of microprojectiles measuring 1 to 4 μm. The expression vector is introduced into plant tissues with a biolistic device that accelerates the microprojectiles to speeds of 300 to 600 m/s which is sufficient to penetrate plant cell walls and membranes. Sanford et al., *Part. Sci. Technol.* 5:27 (1987), Sanford, J. C., *Trends Biotech.* 6:299 (1988), Klein et al., *Bio/Technology* 6:559–563 (1988), Sanford, J. C., *Physiol Plant* 7:206 (1990), Klein et al., *Biotechnology* 10:268 (1992). See also U.S. Pat. No. 5,015,580 (Christou, et al.), issued May 14, 1991; U.S. Pat. No. 5,322,783 (Tomes, et al.), issued Jun. 21, 1994.

Another method for physical delivery of DNA to plants is sonication of target cells. Zhang et al., *Bio/Technology* 9:996 (1991). Alternatively, liposome or spheroplast fusion have been used to introduce expression vectors into plants. Deshayes et al., *EMBO J.*, 4:2731 (1985), Christou et al., *Proc Natl. Acad. Sci. U.S.A.* 84:3962 (1987). Direct uptake of DNA into protoplasts using $CaCl_2$ precipitation, polyvinyl alcohol or poly-L-omithine have also been reported. Hain et al., *Mol. Gen. Genet.* 199:161 (1985) and Draper et al., *Plant Cell Physiol.* 23:451 (1982). Electroporation of protoplasts and whole cells and tissues have also been described. Donn et al., In Abstracts of VIIth International Congress on Plant Cell and Tissue Culture IAPTC, A2-38, p 53 (1990); D'Halluin et al., *Plant Cell* 4:1495–1505 (1992) and Spencer et al., *Plant Mol. Biol.* 24:51–61 (1994).

Following transformation of cotton target tissues, expression of the above-described selectable marker genes allows for preferential selection of transformed cells, tissues and/or plants, using regeneration and selection methods now well known in the art.

The foregoing methods for transformation would typically be used for producing a transgenic variety. The transgenic variety could then be crossed, with another (non-transformed or transformed) variety, in order to produce a new transgenic variety. Alternatively, a genetic trait which has been engineered into a particular cotton line using the foregoing transformation techniques could be moved into another line using traditional backcrossing techniques that are well known in the plant breeding arts. For example, a backcrossing approach could be used to move an engineered trait from a public, non-elite variety into an elite variety, or from a variety containing a foreign gene in its genome into a variety or varieties which do not contain that gene. As used herein, "crossing" can refer to a simple X by Y cross, or the process of backcrossing, depending on the context.

Tissue Culture of Cotton—When the term "cotton plant" is used in the context of the present invention, this also includes any single gene conversions of that variety. The term "single gene converted plant" as used herein refers to those cotton plants which are developed by a plant breeding technique called backcrossing wherein essentially all of the desired morphological and physiological characteristics of a variety are recovered in addition to the single gene transferred into the variety via the backcrossing technique. Backcrossing methods can be used with the present invention to improve or introduce a characteristic into the variety. The term "backcrossing" as used herein refers to the repeated crossing of a hybrid progeny back to the recurrent parent, i.e., backcrossing 1, 2, 3, 4, 5, 6, 7 or more times to the recurrent parent. The parental cotton plant which contributes the gene for the desired characteristic is termed the "nonrecurrent" or "donor parent". This terminology refers to the fact that the nonrecurrent parent is used one time in the backcross protocol and therefore does not recur. The parental cotton plant to which the gene or genes from the nonrecurrent parent are transferred is known as the recurrent parent as it is used for several rounds in the backcrossing protocol (Poehlman & Sleper, 1994; Fehr, 1987). In a typical backcross protocol, the original variety of interest (recurrent parent) is crossed to a second variety (nonrecurrent parent) that carries the single gene of interest to be transferred. The resulting progeny from this cross are then crossed again to the recurrent parent and the process is repeated until a cotton plant is obtained wherein essentially all of the desired morphological and physiological characteristics of the recurrent parent are recovered in the converted plant, in addition to the single transferred gene from the nonrecurrent parent.

The selection of a suitable recurrent parent is an important step for a successful backcrossing procedure. The goal of a backcross protocol is to alter or substitute a single trait or characteristic in the original variety. To accomplish this, a single gene of the recurrent variety is modified or substituted with the desired gene from the nonrecurrent parent, while retaining essentially all of the rest of the desired genetic, and therefore the desired physiological and morphological, constitution of the original variety. The choice of the particular nonrecurrent parent will depend on the purpose of the backcross. One of the major purposes is to add some commercially desirable, agronomically important trait to the plant. The exact backcrossing protocol will depend on the characteristic or trait being altered to determine an appropriate testing protocol. Although backcrossing methods are simplified when the characteristic being transferred is a dominant allele, a recessive allele may also be transferred. In this instance it may be necessary to introduce a test of the progeny to determine if the desired characteristic has been successfully transferred.

Many single gene traits have been identified that are not regularly selected for in the development of a new variety but that can be improved by backcrossing techniques. Single gene traits may or may not be transgenic, examples of these traits include but are not limited to, male sterility, waxy starch, herbicide resistance, resistance for bacterial, fungal, or viral disease, insect resistance, male fertility, enhanced nutritional quality, industrial usage, yield stability and yield enhancement. These genes are generally inherited through the nucleus. Several of these single gene traits are described in U.S. Pat. Nos. 5,959,185, 5,973,234 and 5,977,445, the disclosures of which are specifically hereby incorporated by reference.

Further reproduction of the variety can occur by tissue culture and regeneration. Tissue culture of various tissues of cotton and regeneration of plants therefrom is well known and widely published. For example, reference may be had to Komatsuda, T. et al., "Genotype X Sucrose Interactions for Somatic Embryogenesis in Soybean," *Crop Sci*. 31:333–337 (1991); Stephens, P. A., et al., "Agronomic Evaluation of Tissue-Culture-Derived Soybean Plants," *Theor. Appl. Genet.* (1991) 82:633–635; Komatsuda, T. et al., "Maturation and Germination of Somatic Embryos as Affected by Sucrose and Plant Growth Regulators in Soybeans *Glycine gracilis* Skvortz and *Glycine max* (L.) Merr." *Plant Cell, Tissue and Organ Culture*, 28:103–113 (1992); Dhir, S. et al., "Regeneration of Fertile Plants from Protoplasts of Soybean (*Glycine max* L. Merr.); Genotypic Differences in Culture Response," *Plant Cell Reports* (1992) 11:285–289; Pandey, P. et al., "Plant Regeneration from Leaf and Hypocotyl Explants of *Glycine-wightii* (W. and A.) VERDC. var. longicauda," *Japan J. Breed*. 42:1–5 (1992); and Shetty, K., et al., "Stimulation of In Vitro Shoot Organogenesis in *Glycine max* (Merrill.) by Allantoin and Amides," *Plant Science* 81:245–251 (1992); as well as U.S. Pat. No. 5,024,944 issued Jun. 18, 1991 to Collins et al., and U.S. Pat. No. 5,008,200 issued Apr. 16, 1991 to Ranch et al., the disclosures of which are hereby incorporated herein in their entirety by reference. Thus, another aspect of this invention is to provide cells which upon growth and differentiation produce cotton plants having the physiological and morphological characteristics of cotton variety 00S07.

As used herein, the term "tissue culture" indicates a composition comprising isolated cells of the same or a different type or a collection of such cells organized into parts of a plant. Exemplary types of tissue cultures are protoplasts, calli, plant clumps, and plant cells that can generate tissue culture that are intact in plants or parts of plants, such as embryos, pollen, flowers, seeds, pods, leaves, stems, roots, root tips, anthers, and the like. Means for preparing and maintaining plant tissue culture are well known in the art. By way of example, a tissue culture comprising organs has been used to produce regenerated plants. U.S. Pat. Nos. 5,959,185, 5,973,234 and 5,977,445, described certain techniques, the disclosures of which are incorporated herein by reference.

This invention also is directed to methods for producing a cotton plant by crossing a first parent cotton plant with a second parent cotton plant wherein the first or second parent cotton plant is a cotton plant of the variety 00S07. Further, both first and second parent cotton plants can come from the cotton variety 00S07. Thus, any such methods using the cotton variety 00S07 are part of this invention: selfing, backcrosses, hybrid production, crosses to populations, and the like. All plants produced using cotton variety 00S07 as a parent are within the scope of this invention, including those developed from varieties derived from cotton variety 00S07. Advantageously, the cotton variety could be used in crosses with other, different, cotton plants to produce first generation ($F_1$) cotton hybrid seeds and plants with superior characteristics. The variety of the invention can also be used for transformation where exogenous genes are introduced and expressed by the variety of the invention. Genetic variants created either through traditional breeding methods using variety 00S07 or through transformation of 00S07 by any of a number of protocols known to those of skill in the art are intended to be within the scope of this invention.

As shown in Table 2 below, 00S07 is compared to other cotton varieties. Column one shows the varieties, column 2 gives the yield of lint in pounds per acre (Yield), column 3 shows the lint percent (Lint %), columns 4 and 5 provide the micronaire (Mic) and fiber length (Len), columns 6, 7 and 8 show the uniformity ratio (UR), fiber strength (T1) and fiber elongation (E1), columns 9, 10 and 11 give the plant height in inches (Hgt), maturity rating (Mat) and stringout rating (So).

TABLE 2

SUMMARY OF 29 TESTS, 2000–2002

| Variety | Yield | Lint % | Mic | Len | UR | T1 | E1 | Hgt | Mat | So |
|---|---|---|---|---|---|---|---|---|---|---|
| 00S07 | 1274 | 0.388 | 4.02 | 1.201 | 84.24 | 31.92 | 10.68 | 42.36 | 1.95 | 2.74 |
| SG 747 | 1211 | 0.396 | 4.68 | 1.134 | 84.47 | 29.08 | 12.42 | 42.65 | 1.67 | 2.96 |
| Difference | 63 | −0.008 | −0.66 | 0.067 | −0.23 | 2.84 | −1.74 | −0.29 | 0.28 | −0.22 |

DEPOSIT INFORMATION

A deposit of the D&PL Technology Holding Company. LLC proprietary cotton cultivar designated 00S07 disclosed above and recited in the appended claims has been made with the American Type Culture Collection (ATCC), 10801 University Boulevard, Manassas, Va. 20110. The date of deposit was Feb. 18, 2005. The deposit of 2,500 seeds was taken from the same deposit maintained by D&PL Technology Holding Company, LLC since prior to the filing date of this application. All restrictions upon the deposit have been removed, and the deposit is intended to meet all of the requirements of 37 C.F.R. 1.801–1.809. The ATCC accession number is PTA-6594. The deposit will be maintained in the depository for a period of 30 years or 5 years after the last reguest, or for the effective life of the patent, whichever is longer, and will be replaced as necessary during that period.

Although the foregoing invention has been described in some detail by way of illustration and example for purposes of clarity and understanding, it will be obvious that certain changes and modifications may be practiced within the scope of the invention, as limited only by the scope of the appended claims.

What is claimed is:

1. A seed of cotton cultivar designated 00S07, wherein a representative sample of seed of said cultivar was deposited under ATCC Accession No. PTA-6594.

2. A cotton plant, or a part thereof, produced by growing the seed of claim 1.

3. A tissue culture of regenerable cells produced from the plant of claim 2.

4. A protoplast produced from the tissue culture of claim 3.

5. The tissue culture of claim 3, wherein said regenerable cells are produced from a plant part selected from the group consisting of leaf, pollen, embryo, root, root tip, anther, flower, boll and stem.

6. A cotton plant regenerated from the tissue culture of claim 3, wherein said plant has all the morphological and physiological characteristics of cultivar 00S07, representative sample of seed of said cultivar having been deposited under ATCC Accession No. PTA-6594.

7. A method for producing an F1 hybrid cotton seed, comprising crossing the plant of claim 2 with a different cotton plant and harvesting the resultant F1 hybrid cotton seed.

8. A method for producing a male sterile cotton plant comprising transforming the cotton plant of claim 2 with a nucleic acid molecule that confers male sterility.

9. A male sterile cotton plant produced by the method of claim 8. II.

10. A method of producing an herbicide resistant cotton plant comprising transforming the cotton plant of claim 2 with a transgene that confers herbicide resistance.

11. An herbicide resistant cotton plant produced by the method of claim 10.

12. The cotton plant of claim 11, wherein the transgene confers resistance to an herbicide selected from the group consisting of imidazolinone, sulfonylurea, glyphosate, glufosinate, L-phosphinothricin, triazine and benzonitrile.

13. A method of producing an insect resistant cotton plant comprising transforming the cotton plant of claim 2 with a transgene that confers insect resistance.

14. An insect resistant cotton plant produced by the method of claim 13.

15. The cotton plant of claim 14, wherein the transgene encodes a *Bacillus thuringiensis* endotoxin.

16. A method of producing a disease resistant cotton plant comprising transforming the cotton plant of claim 2 with a transgene that confers disease resistance.

17. A disease resistant cotton plant produced by the method of claim 16.

18. A method of producing a cotton plant with modified fatty acid metabolism or modified carbohydrate metabolism comprising transforming the cotton plant of claim 2 with a transgene encoding a protein selected from the group consisting of fructosyltransferase, levansucrase, alpha-amylase, invertase and starch branching enzyme or encoding an antisense of stearyl-ACP desaturase.

19. A cotton plant having modified fatty acid metabolism or modified carbohydrate metabolism produced by the method of claim 18.

20. A cotton plant, or a part thereof, having all the physiological and morphological characteristics of cultivar 00S07, representative sample of seed of said cultivar having been deposited under ATCC Accession No. PTA-6594.

21. A method of introducing a desired trait into cotton cultivar 00S07 comprising:
   (a) crossing 00S07 plants grown from 00S07 seed, wherein a representative sample of seed was deposited under ATCC Accession No. PTA-6594, with plants of another cotton *Gossypium hirsutum* cultivar that comprise a desired trait to produce progeny plants, wherein the desired trait is selected from the group consisting of male sterility, herbicide resistance, insect resistance and disease resistance;
   (b) selecting one or more progeny plants that have the desired trait to produce selected progeny plants;
   (c) crossing the selected progeny plants with the 00S07 plants to produce backcross progeny plants;
   (d) selecting for backcross progeny plants that have the desired trait and physiological and morphological characteristics of cotton cultivar 00S07 listed in Table 1 to produce selected backcross progeny plants; and
   (e) repeating steps (c) and (d) three or more times in succession to produce selected fourth or higher backcross progeny plants that comprise the desired trait and all of the physiological and morphological characteristics of cotton cultivar 00S07 listed in Table 1.

22. A cotton plant produced by the method of claim 21, wherein the plant has the desired trait and all of the physiological and morphological characteristics of cotton cultivar 00S07 listed in Table 1.

23. The cotton plant of claim 22 wherein the desired trait is herbicide resistance and the resistance is conferred to an herbicide selected from the group consisting of imidazolinone, sulfonylurea, glyphosate, glufosinate, L-phosphinothricin, triazine and benzonitrile.

24. The cotton plant of claim 22 wherein the desired trait is insect resistance and the insect resistance is conferred by a transgene encoding a *Bacillus thuringiensis* endotoxin.

25. The cotton plant of claim 22 wherein the desired trait is male sterility and the trait is conferred by a cytoplasmic nucleic acid molecule that confers male sterility.

* * * * *